United States Patent [19]
Hoffman et al.

[11] Patent Number: 6,087,665
[45] Date of Patent: Jul. 11, 2000

[54] MULTI-LAYERED SCINTILLATORS FOR COMPUTED TOMOGRAPH SYSTEMS

[75] Inventors: David M. Hoffman, New Berlin; Hui David He, Waukesha, both of Wis.

[73] Assignee: General Electric Company, Milwaukee, Wis.

[21] Appl. No.: 08/980,193

[22] Filed: Nov. 26, 1997

[51] Int. Cl.$^7$ .................................................. G01T 1/20
[52] U.S. Cl. ..................... 250/483.1; 250/368; 250/367; 378/19
[58] Field of Search .................................. 250/483.1, 368, 250/367; 378/19

[56] References Cited

U.S. PATENT DOCUMENTS 5,391,879  2/1995  Tran et al. ............................. 250/368
5,594,253  1/1997  Bueno et al. ........................... 250/368

*Primary Examiner*—Constantine Hannaher
*Assistant Examiner*—Andrew Israel
*Attorney, Agent, or Firm*—Armstrong Teasdale; Christian G. Cabou; Phyllis Y. Price

[57] ABSTRACT

A multi-layer scintillator having a first and a second layer of scintillation material. In one embodiment, the scintillator first layer has fast scintillation characteristics and the second layer has a higher transparency than the first layer. The two scintillating layers are bonded together so that a light signal is transferred from the first layer to the second layer and the second layer to a photodiode adjacent the second layer. The specific scintillating materials are selected to achieve the desired characteristics of the scintillator.

12 Claims, 3 Drawing Sheets

MULTI-LAYERED SCINTILLATORS FOR COMPUTED TOMOGRAPH SYSTEMS

FIELD OF THE INVENTION

This invention relates generally to computed tomograph imaging and, more particularly, to scintillators utilized in connection with the detection of x-rays in CT imaging.

BACKGROUND OF THE INVENTION

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodiodes adjacent the scintillator.

Known scintillators are fabricated from various scintillating materials. These scintillating materials are divided into specific classes, with each having advantages and disadvantages. For example, some scintillating materials are fast but suffer from low light output, high radiation damage, or low transparency leading to Z-axis non-uniformity. Although it is desirable to utilize the fast scintillating material, the tradeoffs sometimes preclude use of such material.

Accordingly, it would be desirable to provide a scintillator that offers reasonable tradeoffs between speed, output signal magnitude, and other scintillator characteristics. It would also be desirable to provide a scintillator which is capable of self collimating the light transmission in the lateral direction so that a separate collimator is no longer required.

SUMMARY OF THE INVENTION

These and other objects may be attained by a scintillator including a plurality of layers of scintillating materials. The scintillator is configured so that a X-ray beam signal impinges upon a first layer of high speed scintillating material, and then passes through the first layer and travels to a second layer of higher transparency scintillating material. After traveling through the second layer, the signal is received by a photodiode which converts the optical signal from the scintillator element to an electrical signal.

In one embodiment, the scintillator is fabricated by bonding the first layer of scintillating material to the second layer of scintillating material using an optical adhesive. Specifically, the first and second layers of scintillating material are selected and cut to the appropriate size and thickness. The first and second layers are then positioned adjacent one another and bonded together. Selecting a combination of various material types and thicknesses enables the scintillator to produce specific results. In one specific embodiment, one of the layers is formed by a plurality of radiation resistant optical fibers enabling the scintillator to be self-collimating.

The above described scintillator offers reasonable tradeoffs between speed, output signal magnitude, and other scintillator characteristics. The scintillator self collimates light transmission in the lateral direction.

DETAILED DESCRIPTION

Figure 1:
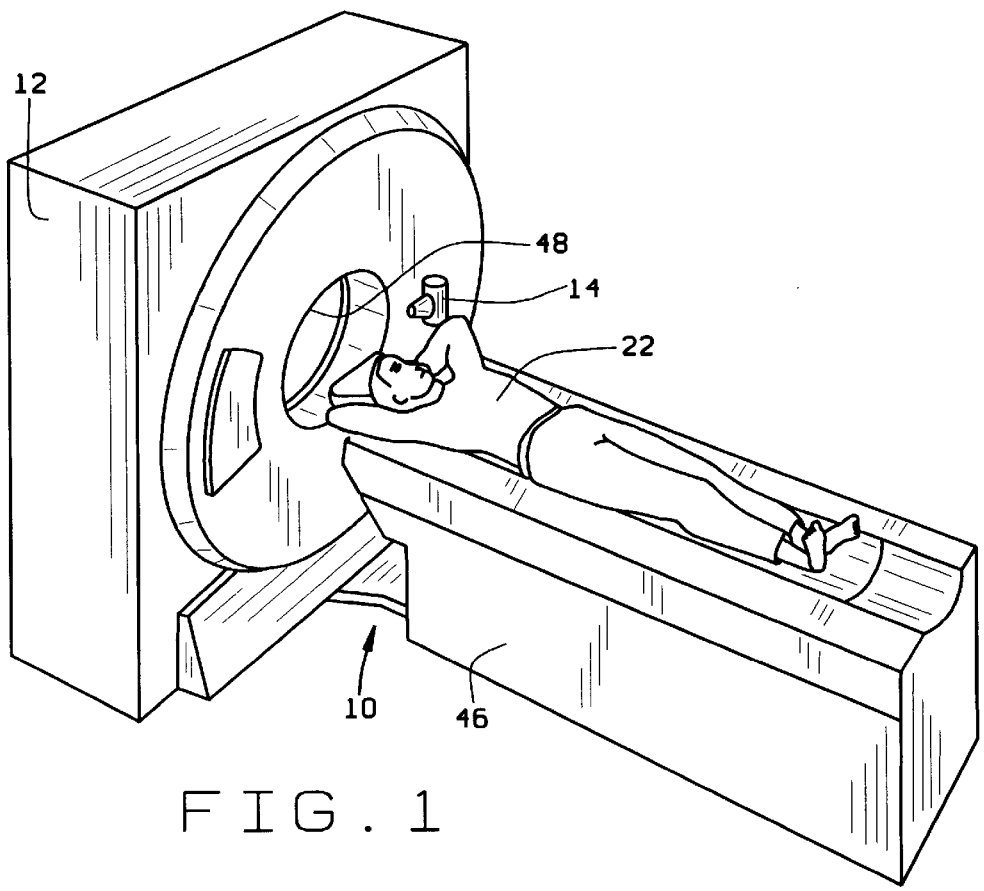
FIG. 1 is a pictorial view of a CT imaging system.
Figure 2:
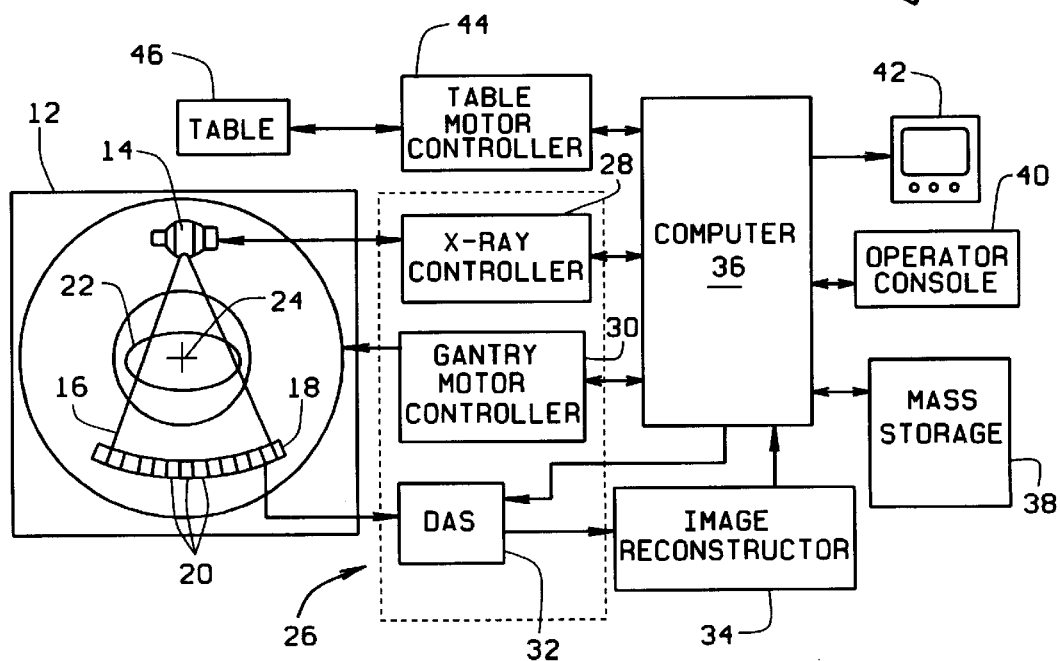
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

As explained above, each detector element 20 of array 18 produces a separate electrical signal that is a measurement of the beam attenuation at the detector location. Particularly, each x-ray detector element 20 typically includes a scintillator element, and adjacent scintillator elements are separated by non-scintillating gaps (not shown). Photodiodes are positioned adjacent the scintillators and generate electrical signals (not shown) representative of the light output by the scintillator elements. The attenuation measurements from all detector elements 18 are acquired separately to produce a transmission profile.

Current scintillator materials (not shown) can be separated into general classes: one class is a fast detector with low light output and high radiation damage and the second class is a fast detector with low transparency leading to Z-axis non-uniformity.

Generally, and with respect to the scintillators described below and constructed in accordance with the present invention, the scintillators are configured to include at least two layers of scintillating material. By providing at least two distinct layers of material, an optimal mix of characteristics can be achieved.

Figure 3:
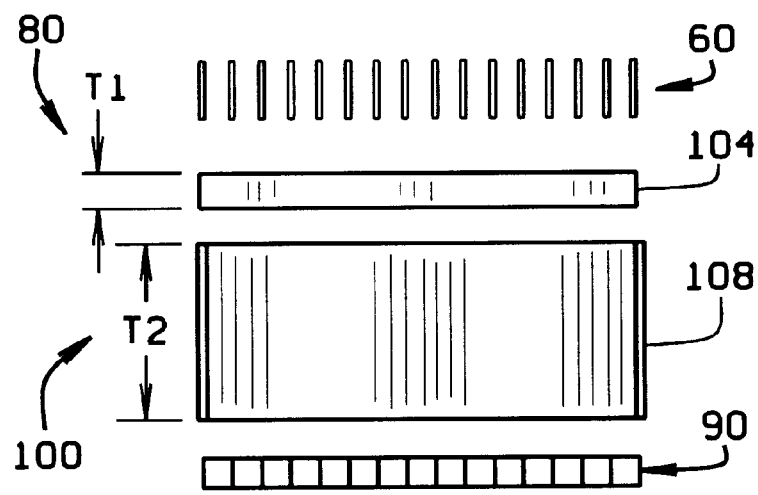
FIG. 3 is a schematic illustration of a multi-layer scintillator in accordance with the present invention prior to coupling the layers.
Figure 4:
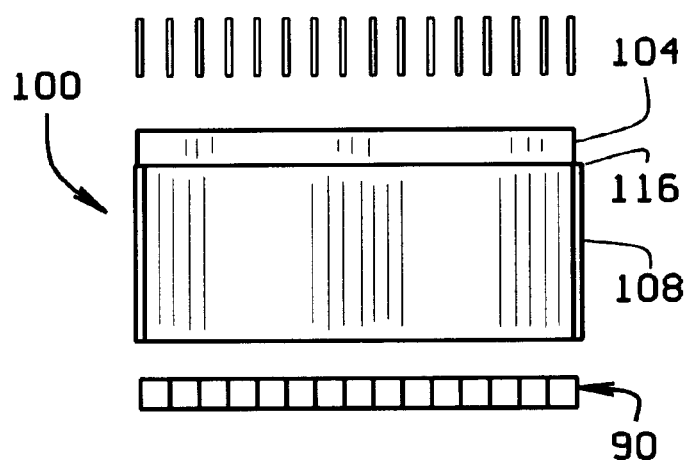
FIG. 4 is a schematic illustration of the multi-layer scintillator shown in FIG. 3 after bonding the scintillation layers.

More particularly, FIG. 3 is a schematic illustration of a portion of a detector 80 including photodiodes 90 and a scintillator 100 having adjacent first and second layers of scintillator material 104 and 108. Scintillator 100 is configured so that X-ray beams 16 (not shown in FIG. 3) impinge upon first layer 104. Second layer 108 is positioned between first layer 104 and photodiodes 90.

In one embodiment, first layer 104 has fast scintillation characteristics, for example, GOS ($Gd_2O_3S$), and a thickness T1, for example, about 0.5 mm. Second layer 108 has a thickness T2 and a higher transparency characteristic than first layer 104. Second layer 108 is, for example, Lumex $(YGd)_2O_3$ material having a thickness T2 of approximately 1.5 to 2.0 mm. Scintillator 100 is very fast, has a very high output level, as well as an improved Z-axis uniformity.

The materials selected for first and second layers 104 and 108 may include other scintillating materials. For example, the material for first layer 104 may be selected from scintillating materials having a high light output and the material for second layer 108 may be scintillating material having a lower radiation damage factor than first layer 104 or a high uniformity factor. The specific scintillating materials selected depend upon the specific characteristics desired for scintillator 100 and detector 80.

In an alternative embodiment, first and second layers 104 and 108 are selected from a variety of materials other than two scintillation materials including, for example, one scintillation material layer and an X-ray absorbing light conducting layer, or a film screen material layer and a scintillator layer, or the film screen material and an X-ray absorbing layer (not shown). For example, the light absorbing layer would act as a light pipe and provide photodiodes 90 with protection from X-rays 16. In addition, first and second layers 104 and 108 may be other materials including, for example, a scintillator layer and a scintillating or non-scintillating dense glass.

In fabricating scintillator 100, the materials for first layer 104 and second layer 108 are selected and cut to the appropriate size and thickness. First and second layers 104 and 108 may be coupled together in a variety of manners including, for example, bonding, sintering, optical adhesives, optical liquids, or directly grown on each other. If, for example, an optical adhesive 116 is selected to bond first and second layers 104 and 108, optical adhesive 116 is applied to an upper surface of second layer 108 prior to placing first layer 104 adjacent to second layer 108. Selection of the specific composition of adhesive 116 varies depending upon the selection of the first and second layers 104 and 108 and the desired characteristics of scintillator 100. After coupling first and second layers 104 and 108, scintillator is processed into a detector (not shown) in a manner known in the art.

Figure 5:
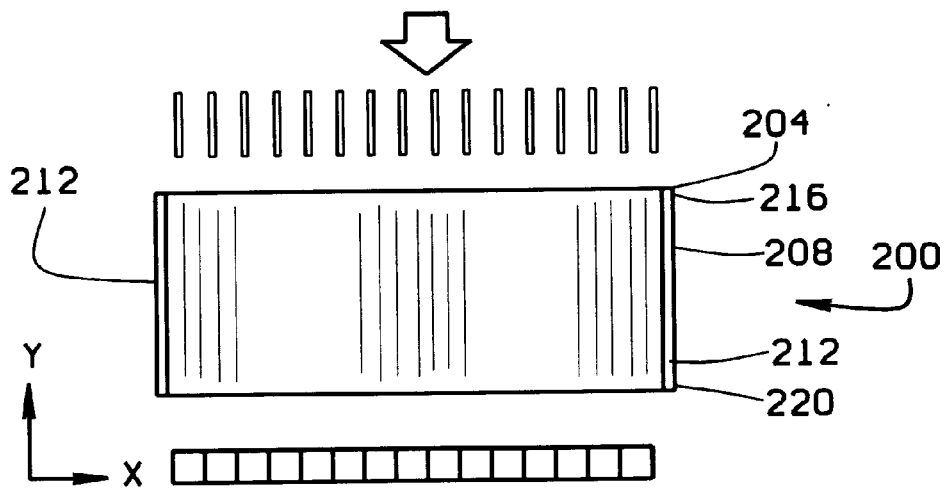
FIG. 5 is a schematic illustration of an alternative embodiment of the scintillator shown in FIG. 3.

In an alternative embodiment shown in FIG. 5, scintillator 200 includes a first layer 204 of scintillating material and a second layer 208 formed by a plurality of radioluminescent optical fibers 212. Radiation resistant optical fibers 212 each have an input end 216 and an output end 220. First layer of scintillating material 204 is coupled to second layer 208 as described above, or is doped directly on fiber input ends 216. For example, the small diameter and light reflection characteristics of fibers 212 allow scintillator 200 to self collimate the light transmission in the lateral direction. This self-collimation enables lateral spatial resolution to be maintained throughout scintillitor 200.

Figure 6:
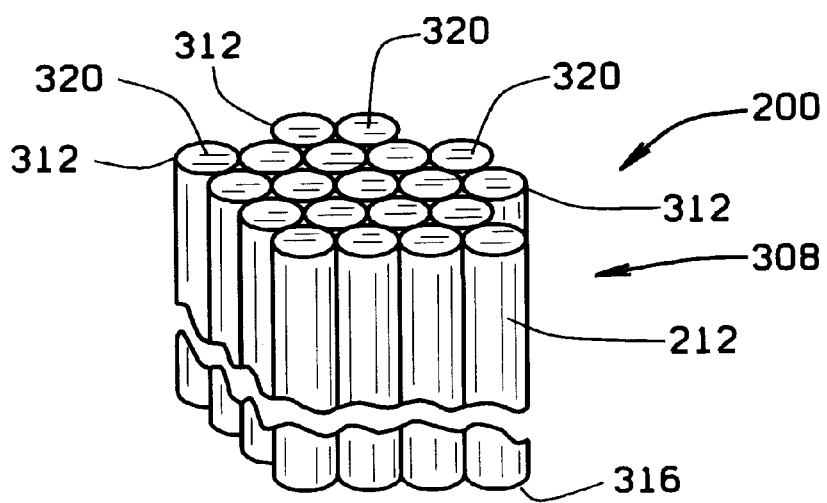
FIG. 6 is perspective view of the optical fibers scintillator illustrated in FIG. 5.

In one specific embodiment of scintillator 200, and referring to FIG. 6, optical fibers 212 are arranged in a bundle 308. Bundle 308 has an input end 312 and an output end 316. First layer of x-ray scintillating material 320 is optically coupled to input end 312. First layer 320 may be fabricated as a single layer (not shown) which covers entire bundle 308 or as a plurality of pieces which cover individual input ends 312, for example, by doping input ends 312 with an X-ray scintillating material 320.

The above described scintillators include a plurality of scintillation material layers to optimize specific characteristics of the device. The described scintillators may be fabricated so that the specific advantages of several different types of materials are combined. In addition, the scintillator may collimate the light transmission in the lateral direction.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Specifically, although only two layers were described above, the number of layers is not limited and any number of layers can be coupled to achieve the specific result sought. Accordingly, the spirit and scope of the invention are to be limited only by the terms of the appended claims.

What is claimed is:

1. A scintillator for a computed tomograph machine, said scintillator comprising:
    a first layer of material having a fast scintillation characteristic; and
    a second layer of material other than an optical fiber having a higher transparency characteristic than said first layer.

2. A scintillator in accordance with claim 1 wherein said first material layer comprises GOS.

3. A scintillator in accordance with claim 2 wherein said first material layer has a thickness of about 0.5 mm.

4. A scintillator in accordance with claim 1 wherein said second material layer comprises $(YGd)_2O_3$.

5. A scintillator in accordance with claim 1 wherein said scintillator is configured so that x-ray beams impinge on said first material layer.

6. A scintillator in accordance with claim 1 wherein said first material layer is bonded to said second material layer.

7. A scintillator in accordance with claim 1 wherein said first material layer is sintered to said second material layer.

8. A scintillator in accordance with claim 1 wherein said first material layer is a film screen material.

9. A scintillator in accordance with claim 1 wherein said first layer is grown directly on top of said second layer.

10. A scintillator for a computed tomograph machine, said scintillator comprising:
   a first layer of material having a fast scintillation characteristic; and
   a second layer having a higher transparency characteristic than said first layer;
   wherein said first material layer is sintered to said second material layer.

11. A scintillator for a computed tomograph machine, said scintillator comprising:
   a first layer of material comprising GOS and having a fast scintillation characteristic; and
   a second layer consisting essentially of $(YGd)_2O_3$ and having a higher transparency characteristic than said first layer.

12. A scintillator in accordance with claim 1 wherein said scintillator comprises additional layers of material.

* * * * *